US00PP20258P2

(12) United States Plant Patent
Klemm

(10) Patent No.: US PP20,258 P2
(45) Date of Patent: Sep. 1, 2009

(54) ***DIASCIA* PLANT NAMED 'KLEDB06039'**

(50) Latin Name: *Diascia ×hybrida*
Varietal Denomination: KLEDB06039

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 35 days.

(21) Appl. No.: 12/002,454

(22) Filed: Dec. 17, 2007

(51) Int. Cl.
*A01H 5/00* (2006.01)

(52) U.S. Cl. ..... Plt./425

(58) Field of Classification Search ..... Plt./263, Plt./425

See application file for complete search history.

*Primary Examiner*—Susan B McCormick Ewoldt
(74) *Attorney, Agent, or Firm*—C. A. Whealy

(57) ABSTRACT

A new and distinct cultivar of *Diascia* plant named 'KLEDB06039' characterized by its vigorous growth habit; freely branching habit; freely flowering habit; and large violet blue-colored flowers.

1 Drawing Sheet

Botanical designation: *Diascia×hybrida.*
Cultivar denomination: 'KLEDB06039'.

BACKGROUND OF THE INVENTION

The present invention relates to a new and distinct cultivar of *Diascia,* botanically known as *Diascia×hybrida,* and hereinafter referred to by the name 'KLEDB06039'.

The new *Diascia* is a product of a planned breeding program conducted by the Inventor in Stuttgart, Germany The objective of the breeding program is to create new compact *Diascia* cultivars with uniform plant habit, large flowers and attractive flower colors.

The new *Diascia* originated from a cross-pollination made by the Inventor in Stuttgart, Germany in June, 2004 of a proprietary selection of *Diascia×hybrida* identified as code number X 075, not patented, as the female, or seed, parent with a proprietary selection of *Diascia×hybrida* identified as code number X 140, not patented, as the male, or pollen, parent. The cultivar KLEDB06039 was discovered and selected by the Inventor as a flowering plant within the progeny of the stated cross-pollination in a controlled environment in Stuttgart, Germany in May, 2005.

Asexual reproduction of the new *Diascia* by terminal cuttings in a controlled environment in Stuttgart, Germany since September, 2005, has shown that the unique features of this new *Diascia* are stable and reproduced true to type in successive generations.

SUMMARY OF THE INVENTION

The cultivar KLEDB06039 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'KLEDB06039'. These characteristics in combination distinguish 'KLEDB06039' as a new and distinct cultivar of *Diascia:*

1. Vigorous growth habit.
2. Freely branching habit.
3. Freely flowering habit.
4. Large violet blue-colored flowers.

Plants of the new *Diascia* can be compared to plants of the female parent selection. Plants of the new *Diascia* differ from plants of the female parent selection in the following characteristics:

1. Plants of the new *Diascia* are more vigorous than plants of the female parent selection.
2. Plants of the new *Diascia* have larger flowers than plants of the female parent selection.
3. Plants of the new *Diascia* and the female parent selection differ in flower color as plants of the female parent selection have pinkish blue-colored flowers.

Plants of the new *Diascia* can be compared to plants of the male parent selection. Plants of the new *Diascia* differ from plants of the male parent selection in the following characteristics:

1. Plants of the new *Diascia* have larger flowers than plants of the male parent selection.
2. Plants of the new *Diascia* and the male parent selection differ in flower color as plants of the male parent selection have bluish pink-colored flowers.

Plants of the new *Diascia* can be compared to plants of the *Diascia×hybrida* cultivar Darea Deep Salmon, not patented. In side-by-side comparisons conducted in Stuttgart, Germany, plants of the new *Diascia* differed from plants of the cultivar Darea Deep Salmon in the following characteristics:

1. Plants of the new *Diascia* were not as compact as plants of the cultivar Darea Deep Salmon.
2. Flowers of plants of the new *Diascia* and the cultivar Darea Deep Salmon differed in flower color as plants of the cultivar Darea Deep Salmon had dark salmon-colored flowers.

BRIEF DESCRIPTION OF THE PHOTOGRAPH

The accompanying colored photograph illustrates the overall appearance of the new *Diascia*, showing the colors as true as it is reasonably possible to obtain in colored reproductions of this type. Colors in the photograph may differ slightly from the color values cited in the detailed botanical description which accurately describe the colors of the new *Diascia.* The photograph comprises a close-up view of a typical flowering plant of 'KLEDB06039'.

DETAILED BOTANICAL DESCRIPTION

The aforementioned photograph and following observations, measurements and values describe plants grown in Stuttgart, Germany in 11-cm containers in a glass-covered greenhouse during the spring and under conditions which closely approximate commercial production. During the production of the plants, day temperatures ranged from 15° C. to 35° C., night temperatures ranged from 10° C. to 20° C. and maximum light levels were 70,000 lux. Plants were pinched one time and were about four months old when the photograph and the description were taken. In the description, color references are made to The Royal Horticultural Society Colour Chart, 1995 Edition, except where general terms of ordinary dictionary significance are used.

Botanical classification: *Diascia×hybrida* cultivar KLEDB06039.

Parentage:

*Female, or seed, parent.*—Proprietary selection of *Diascia×hybrida* identified as code number X 075, not patented.

*Male or pollen parent.*—Proprietary selection of *Diascia×hybrida* identified as code number X 140, not patented.

Propagation:

*Type.*—By terminal vegetative cuttings.

*Time to initiate roots, summer.*—About five days at temperatures of 25° C.

*Time to initiate roots, winter.*—About eight days at temperatures of 25° C.

*Time to develop roots, summer.*—About ten days at temperatures of 25° C.

*Time to develop roots, winter.*—About 14 days at temperatures of 25° C.

*Root description.*—Fine, fibrous; pale white in color.

*Rooting habit.*—Freely branching; dense.

Plant description:

*Plant form and growth habit.*—Compact, upright and somewhat outwardly spreading plant habit; mounding. Vigorous growth habit.

*Branching habit.*—Freely branching with numerous lateral branches develop per plant; pinching enhances branching.

*Plant height.*—About 20 cm to 28 cm.

*Plant diameter* (*area of spread*).—About 55 cm.

Lateral branch description:

*Length.*—About 25 cm.

*Diameter.*—About 1 mm.

*Internode length.*—About 0.5 cm to 2.5 cm.

*Texture.*—Sparsely pubescent.

*Color.*—137A.

Foliage description:

*Arrangement.*—Alternate, simple.

*Length.*—About 2 cm.

*Width.*—About 1 cm.

*Shape.*—Lanceolate.

*Apex.*—Cuspidate.

*Base.*—Cordate.

*Margin.*—Serrate.

*Texture, upper and lower surfaces.*—Smooth, glabrous.

*Venation pattern.*—Pinnate; arcuate.

*Color.*—Developing foliage, upper surface: 141C. Developing foliage, lower surface: 141D. Fully expanded foliage, upper surface: 141A; venation, 141A. Fully expanded foliage, lower surface: 141D; venation, 141B.

*Petiole.*—Length: About 2.5 mm. Diameter: About 0.5 mm. Texture, upper and lower surfaces: Smooth, glabrous. Color, upper and lower surfaces: 141B.

Flower description:

*Flower arrangement.*—Single flowers arranged on terminal racemes. Freely flowering habit with usually about 12 open flowers and flower buds per lateral branch. Flowers face outwardly. Flowers not fragrant.

*Natural flowering season.*—Plants flower continuously from May through September in Germany. Flowers last about five days on the plant. Flowers not persistent.

*Flower diameter.*—About 1.5 cm.

*Flower length* (*height*).—About 5 mm.

*Flower bud.*—Length: About 2 mm to 5 mm. Diameter: About 2 mm to 5 mm. Shape: Rounded. Color: Between 91C and 69A.

*Petals.*—Arrangement: Corolla consists of five petals modified into two banner petals, two lateral petals with spurs and a protruding lip petal. Length: About 1 cm. Width: About 1 cm. Shape: Obovate. Apex: Obtuse. Base: Attenuate. Margin: Entire. Texture, upper and lower surfaces: Smooth, glabrous, satiny. Color: When opening, upper surface: 83A. When opening, lower surface: Between 83A and 83D. Fully opened, upper surface: 93B; color becoming closer to 93D with development. Fully opened, lower surface: Between 93D and 83D.

*Sepals.*—Appearance: Five sepals fused into a star-shaped calyx. Length: About 3 mm. Width: About 1 mm. Shape: Lanceolate. Apex: Cuspidate. Margin: Entire. Texture, upper and lower surfaces: Smooth, glabrous. Color, upper and lower surfaces: 137A.

*Peduncles.*—Length: About 1.5 cm. Diameter: About 0.5 mm. Angle: Erect. Strength: Strong. Texture: Smooth. Color: 141A.

*Pedicels.*—Length: About 1 cm. Diameter: About 3 mm. Angle: Erect. Strength: Moderately strong. Texture: Smooth. Color: 137A.

*Reproductive organs.*—Androecium: Stamen number: About four. Anther shape: Ovate. Anther length: About 1 mm. Anther color: 150A. Amount of pollen: Moderate. Pollen color: 150A. Gynoecium: Pistil length: About 2 mm. Style length: About 2 mm. Style color: 144C. Stigma appearance: Rounded. Stigma color: 144D. Ovary color: 144C.

*Seeds.*—Length: About 1 mm. Diameter: About 1 mm. Color: Close to 177A.

Temperature tolerance: Plants of the new *Diascia* have been observed to tolerate temperatures from about 2° C. to about 35° C.

Pathogen/pest resistance: Plants of the new *Diascia* have not been shown to be resistant to pathogens and pests common to *Diascia.*

It is claimed:

1. A new and distinct *Diascia* plant named 'KLEDB06039' as illustrated and described.

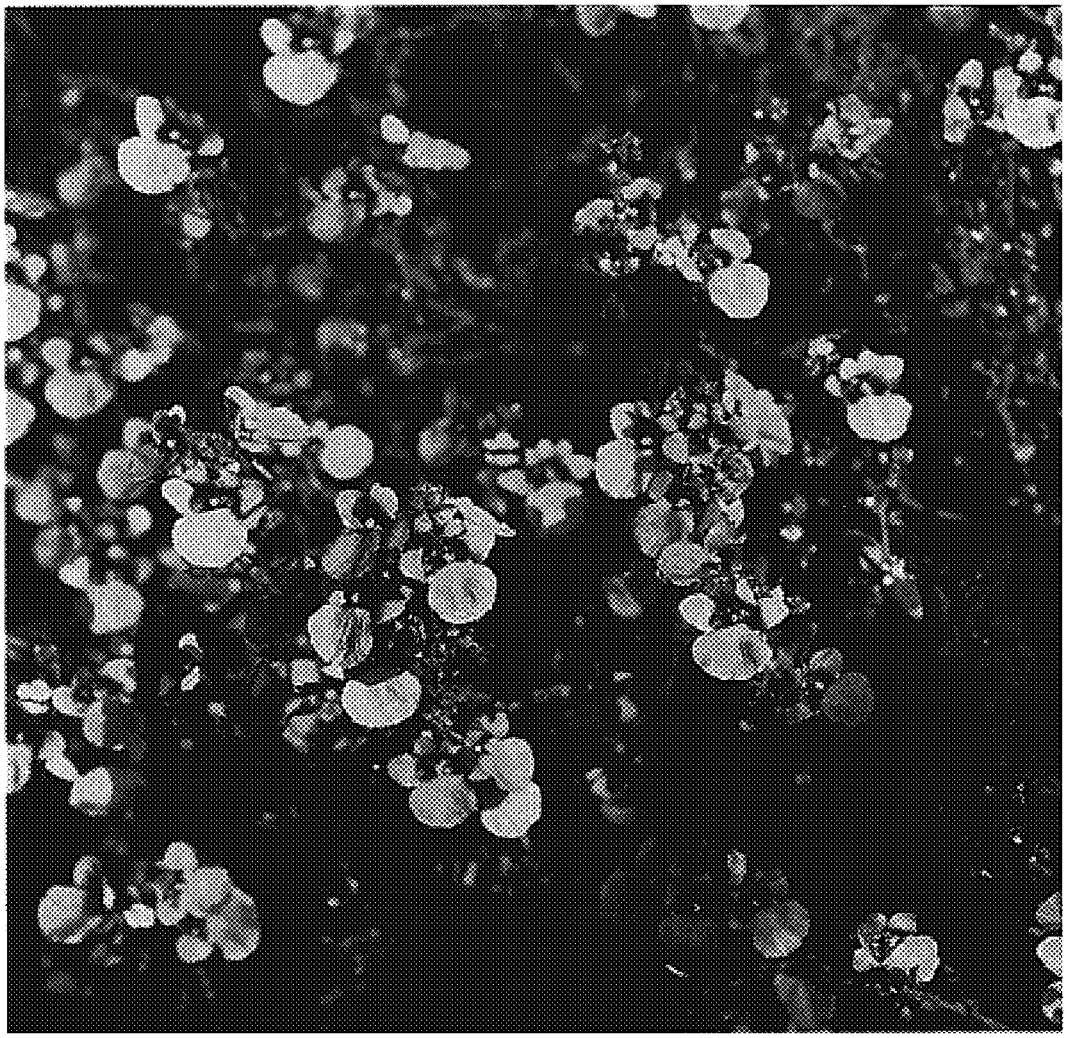

* * * * *